(12) United States Patent
Tallavarjula et al.

(10) Patent No.: US 9,865,438 B2
(45) Date of Patent: Jan. 9, 2018

(54) METHOD AND APPARATUS FOR CALIBRATING OPTICAL PATH DEGRADATION USEFUL FOR DECOUPLED PLASMA NITRIDATION CHAMBERS

(75) Inventors: Sairaju Tallavarjula, Santa Clara, CA (US); Kailash Pradhan, Campbell, CA (US); Huy Q. Nguyen, San Jose, CA (US); Jian Li, Fremont, CA (US)

(73) Assignee: Applied Materials, Inc., Santa Clara, CA (US)

( * ) Notice: Subject to any disclaimer, the term of this patent is extended or adjusted under 35 U.S.C. 154(b) by 459 days.

(21) Appl. No.: 13/188,866

(22) Filed: Jul. 22, 2011

(65) Prior Publication Data

US 2012/0015455 A1 Jan. 19, 2012

Related U.S. Application Data

(62) Division of application No. 12/247,468, filed on Oct. 8, 2008, now Pat. No. 8,101,906.

(51) Int. Cl.
*G12B 13/00* (2006.01)
*H01J 37/32* (2006.01)
(Continued)

(52) U.S. Cl.
CPC ........... *H01J 37/32972* (2013.01); *G01J 3/28* (2013.01); *G01J 3/443* (2013.01); *G01N 21/274* (2013.01);
(Continued)

(58) Field of Classification Search
USPC ..................................................... 250/252.1
See application file for complete search history.

(56) References Cited

U.S. PATENT DOCUMENTS 5,029,245 A 7/1991 Keranen et al.
5,759,242 A 6/1998 Smolarek et al.
(Continued)

FOREIGN PATENT DOCUMENTS

JP 2003-179035 6/2003
JP 2004-039805 2/2004

OTHER PUBLICATIONS

International Search Report and Written Opinion for PCT/US2009/060008, dated May 20, 2010, 11 pp.

*Primary Examiner* — David Porta
*Assistant Examiner* — Shun Lee
(74) *Attorney, Agent, or Firm* — Servilla Whitney LLC

(57) ABSTRACT

Methods for matching semiconductor processing chambers using a calibrated spectrometer are disclosed. In one embodiment, plasma attributes are measured for a process in a reference chamber and a process in an aged chamber. Using a calibrated light source, an optical path equivalent to an optical path in a reference chamber and an optical path in an aged chamber can be compared by determining a correction factor. The correction factor is applied to adjust a measured intensity of plasma radiation through the optical path in the aged chamber. Comparing a measured intensity of plasma radiation in the reference chamber and the adjusted measured intensity in the aged chamber provide an indication of changed chamber conditions. A magnitude of change between the two intensities can be used to adjust the process parameters to yield a processed substrate from the aged chamber which matches that of the reference chamber.

8 Claims, 6 Drawing Sheets

(51) Int. Cl.
*G01J 3/28* (2006.01)
*G01J 3/443* (2006.01)
*G01N 21/27* (2006.01)
*G01N 21/66* (2006.01)

(52) U.S. Cl.
CPC ........ *H01J 37/32935* (2013.01); *G01N 21/66* (2013.01); *H01J 2237/2482* (2013.01)

(56) References Cited

U.S. PATENT DOCUMENTS

| | | |
|---|---|---|
| 6,368,975 B1 | 4/2002 | Balasubramhanya et al. |
| 6,413,867 B1 | 7/2002 | Sarfaty |
| 6,455,437 B1 | 9/2002 | Davidow et al. |
| 6,896,763 B2 | 5/2005 | Balasubramhanya et al. |
| 7,112,763 B2 | 9/2006 | Hunter et al. |
| 7,169,625 B2 | 1/2007 | Davis et al. |
| 2005/0173375 A1 | 8/2005 | Mitrovic et al. |
| 2008/0078504 A1 | 4/2008 | Vukovic |

500     Plasma Matching Between Chambers

502 Calibrate at least one spectrometer using at least one standardized light source.

504 Process a substrate in a reference plasma chamber, record the optical emission spectra using a calibrated spectrometer, and calculate the ratio of the intensities of the selected wavelengths against the total intensity.

506 Process another substrate in a different plasma chamber using the same parameters, record the optical emission spectra during the processing using a calibrated spectrometer, and calculate the ratio of the intensities of the selected wavelengths against the total intensity.

508 Measure the desired surface characteristics on both substrates.

510 Compare the differences in the calculated intensity ratios for both chambers as a function of the surface characteristics.

512 Vary the operating parameters, one at a time, and process a substrate. Collect OES data and surface characteristic data for each set of operating conditions.

514 Using the sensitivities to each of the parameters, determine which operating parameters need to be optimized for chamber matching.

516 Modify the parameters of the second chamber to get the same substrate surface characteristics as the reference chamber.

*Fig 5.*

METHOD AND APPARATUS FOR CALIBRATING OPTICAL PATH DEGRADATION USEFUL FOR DECOUPLED PLASMA NITRIDATION CHAMBERS

CROSS-REFERENCE TO RELATED APPLICATIONS

This application is a divisional of U.S. patent application Ser. No. 12/247,468, filed on Oct. 8, 2008, the contents of which is specifically incorporated by reference herein in its entirety.

TECHNICAL FIELD

The present invention pertains to semiconductor substrate processing chambers. More particularly, techniques for matching a substrate processing chamber parameter setting with an earlier parameter setting of the chamber are disclosed. Additionally, techniques to monitor the plasma stability of a process chamber over a period of time are disclosed.

BACKGROUND ART

Within the semiconductor industry, an ever present need exists for improved process repeatability and control. As new generations of integrated circuits employ smaller feature sizes than were contemplated in previous generations, greater demands are placed on the integrated circuit fabrication process. Deposition and etching of one or more layers on a semiconductor substrate in a plasma environment are two of the most common steps in integrated circuit manufacturing. In addition plasma assisted doping (by implantation of species or incorporation of species are being used extensively in the transistor fabrication. Considering that many discrete plasma processing chambers are employed in either the same manufacturing facility or different manufacturing facilities to manufacture products intended to have the same properties, it is very important that a consistent result is produced from one chamber to another chamber either in the same facility or a different facility. Therefore, to ensure that a consistent film is deposited or etched on the substrate, it is important to make sure that the various plasma processing chambers operate substantially in the same manner.

To ensure that a correct amount and quality of film is deposited, etched, implanted or incorporated, a production process chamber needs to be calibrated against a "reference" chamber (which may also be referred to as a "good" chamber or "golden" chamber). The procedure used to compare chambers is sometimes called chamber qualification. Chamber qualification procedures are used at various times during a chamber's use. When a process chamber is newly manufactured, the chamber must be qualified. The new chamber is typically matched to a "golden" chamber to ensure the new chamber will perform according to its specification. Once the chamber is qualified, the chamber can then be shipped to a semiconductor manufacturing facility. Once the chamber arrives at the semiconductor manufacturing facility, the chamber is reassembled and "qualified" again prior to processing the production materials. In addition, production chambers must undergo regular maintenance or cleaning. After maintenance or chamber cleaning, the chamber needs to be "qualified" again prior to running production wafers. Stringent chamber matching techniques that utilize comprehensive plasma monitoring are needed to ensure process repeatability and control in semiconductor manufacturing.

To ensure that a consistent substrate processing occurs in different chambers, each plasma processing chamber is typically matched to a reference "golden" chamber. The plasma state of the chamber during processing needs to match that of a selected process in a "reference" chamber to ensure the chamber and process are functioning as expected. If the plasma state of the process chamber does not match that of a selected "reference" chamber, the processing parameters can be modified to obtain a matching plasma state, resulting in equivalent products.

Besides chamber matching, monitoring a single chamber over a period of time will decrease chamber downtime. By monitoring the plasma state, the operator can predict when a process will result in product which is outside of the acceptable ranges. This will allow for the determination of when preventative maintenance must be performed on the plasma chamber prior to generating products which do not meet the acceptance criteria.

During a plasma process, certain plasma "attributes", such as the plasma's electromagnetic emissions, the RF power delivered to a wafer pedestal, wafer reflectance, process pressure and process temperature, manifest low frequency fluctuations that contain significant information about the plasma process and the plasma chamber. These attributes affect the resultant process, thereby giving different substrates different surface characteristics. The intensity of a plasma's optical emission spectra (OES) during plasma processing contains information related to the process state, process event and process chamber. OES states are affected to different degrees by varying chamber conditions and by process parameter changes.

Intensities of radiation created during plasma processing are measured through a viewing port in a wall of the processing chamber containing a window, which may be a quartz window. The processing cycles in the chamber may affect the quality of a window in a viewing port, for instance by changing the optical attenuation of the window for a certain wavelength of radiation. The modified attenuation of the window affects the radiation intensity measured by a detector such as a spectrometer compared to an intensity measured from radiation through a clean or unused window. In situations wherein attenuation of a window has changed over previous conditions an uncertainty has been introduced into the accuracy of determining the correct parameter settings based on measuring plasma radiation. One may no longer be sure if a change in measured radiation intensity is caused by a change in plasma radiation that is caused by for instance drift in parameter settings or by a change in attenuation of a viewing port. If a change of measured intensity is caused by a change in actual plasma radiation and adjustment of parameter settings may be required. If a change in measured radiation is determined to be caused solely by changed attenuation of a view port, no adjustments may be required. Accordingly, methods, systems and kits are required to determine if a change in measured radiation is caused by changed processing conditions are required. Kits, systems and methods to adjust process parameter settings for process chambers based on radiation measured through an optical path that has changed over time are also required.

SUMMARY

One or more embodiments of the invention pertain to methods for matching the plasma states of different processing chambers to a reference chamber. Additionally, embodiments of the invention also disclose methods for monitoring the stability, both short- and long-term, of a single plasma processing chamber. One or more embodiments of the invention use a standardized light source to calibrate at least one spectrometer. According to one or more embodiments, spectrometers calibrated to the same reference standard assure that the optical emission spectra from various processing chambers are compared to a uniform external standard.

In one embodiment, a method of matching the performance of process chambers, comprises calibrating at least a first spectrometer with at least a first standardized light source and collecting calibration data; collecting optical emission spectroscopy (OES) data using the at least first spectrometer during a first reference process.

In another embodiment of the invention, the plasma OES is monitored to maintain peak operating efficiency of the chamber. Trends in the OES data will predict when a processing chamber will generate a product which does not meet the acceptable dosing levels.

In one embodiment, a method for determining optical path change in a substrate processing chamber including an optical emission spectroscopy measurement system, comprises positioning a light source and a reference spectrometer for measuring optical intensity through a reference window positioned in a reference optical path between the light source and the reference spectrometer; measuring with the reference spectrometer a reference optical intensity of radiation from the light source transmitted through a reference optical path; measuring a second optical intensity of radiation from the light source through at least a second optical path of the chamber, the second optical path causing attenuation to the radiation different from attenuation of the reference optical path; comparing the reference optical intensity with the second optical intensity to obtain a correction factor for the second optical path; measuring through a reference optical path in the chamber a reference optical plasma intensity generated in the substrate processing chamber; measuring through the second optical path of the chamber a second optical plasma intensity generated in the substrate processing chamber; and comparing the second optical plasma intensity adjusted in accordance with the correction factor with the reference optical plasma intensity.

The method may further include adjusting process parameters to match a performance of the chamber with the second optical path to the chamber having the reference optical path.

In one embodiment, the reference optical path contains one optical window. In another embodiment, a reference optical path contains two optical windows.

In another embodiment, the method further comprises using at least two light sources for measuring optical intensity through a reference window, each light source having a wavelength that is representative for a plasma spectrum generated in the chamber. In still another embodiment, the method further includes measuring a reference optical plasma intensity and a second optical plasma intensity for a plurality of power settings of the chamber.

Another aspect of the invention pertains to a kit for adjusting an operational parameter setting in a substrate processing chamber, comprising: a radiation source, radiating with a known intensity at substantially a first wavelength; a radiation detector, calibrated to the first radiation source; a reference optical window, enabled to be placed in a reference optical path between the first radiation source and the radiation detector, the reference window being equivalent to a first window in a first optical path in the substrate processing chamber; and an adjustment table for adjusting the operational parameter based on a value of a plasma radiation generated by the substrate chamber measured through a second optical path and modified in accordance with a correction factor, the correction factor being determined by: measuring with the radiation detector a reference optical intensity of radiation from the radiation source through the reference optical path; measuring with the radiation detector a second optical intensity of radiation from the radiation source through at least a second optical path of the chamber; and comparing the reference optical intensity with the second optical intensity to obtain a correction factor for the second optical path.

In one embodiment, the kit may also comprise a structure to fix a position of the radiation source, the reference window and the radiation detector. The adjustment table can be implemented in a computing device.

Another aspect of the invention pertains to an apparatus for adjusting a parameter setting in a substrate processing chamber, the system comprising: a memory, the memory configured to store and to retrieve data and instructions; a processor, enabled to retrieve instructions from the memory and execute the instructions to: record a measurement with a reference spectrometer a reference optical intensity of radiation from a light source transmitted through a reference optical path; record a measurement of a second optical intensity of radiation from the light source through at least a second optical path of the chamber, the second optical path causing attenuation to the radiation different from attenuation of the reference optical path; compare the reference optical intensity with the second optical intensity to obtain a correction factor for the second optical path; record a measurement through a reference optical path in the chamber of a reference optical plasma intensity generated in the substrate processing chamber; record a measurement through the second optical path of the chamber of a second optical plasma intensity generated in the substrate processing chamber; and compare the second optical plasma intensity adjusted in accordance with the correction factor with the reference optical plasma intensity. In one embodiment of the apparatus, the system is operative to adjust a process parameter to match a performance of the chamber with the second optical path to the chamber having the reference optical path. In another embodiment of the apparatus, the apparatus includes at least two light sources for measuring optical intensity through a reference window, each light source having a wavelength that is representative for a plasma spectrum generated in the chamber. In another embodiment, the apparatus further comprises the processor is enabled to execute instructions to record a measurement of a reference optical plasma intensity and a second optical plasma intensity for a plurality of power settings of the chamber.

BRIEF DESCRIPTION OF THE DRAWINGS

So that the manner in which the features of various embodiments of the invention described herein are attained and can be understood in detail, a more particular description of embodiments of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

FIG. 5 is a flowchart illustrating steps of a method of plasma matching between two different processing chambers;

DETAILED DESCRIPTION

Figure 1:
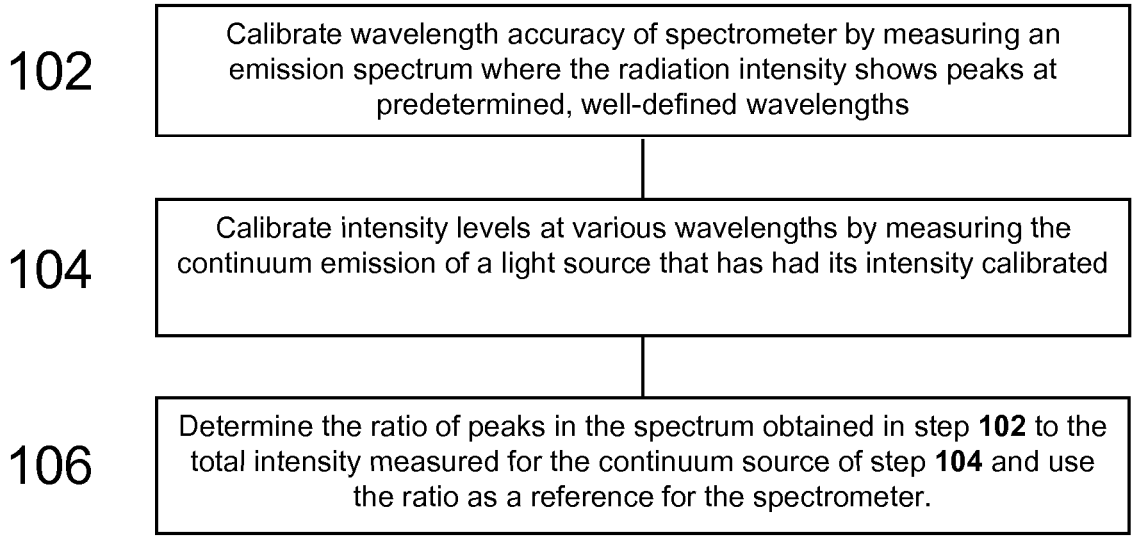
FIG. 1 is a flowchart illustrating the steps of a method for calibrating a spectrometer with primary standard light sources.

Before describing several exemplary embodiments of the invention, it is to be understood that the invention is not limited to the details of construction or process steps set forth in the following description. The invention is capable of other embodiments and of being practiced or being carried out in various ways.

Embodiments of the disclosed invention involve calibrating a spectrometer with at least a primary standard light source, measuring the optical emission spectrum (OES) of a plasma process in a reference processing chamber and the OES of a plasma process in a second processing chamber. According to one or more embodiments, by correlating the plasma emissions with a desired surface characteristic (e.g., nitrogen dose or N-dose during plasma nitridation), the processing parameters of the second chamber are adjusted so the resultant product of the second chamber matches that of the reference chamber. Other embodiments of the disclosed invention involve calibrating a spectrometer with at least a primary standard light source, measuring the OES of a plasma process in which the resultant substrate made by the plasma process has desired characteristics, and continually monitoring the plasma OES for signal drift which would indicate the production of end products not having desired characteristics. While embodiments of the present invention are described herein primarily with reference to nitrogen-based plasma processes (e.g., decoupled plasma nitridation), it will be understood that the principles described herein can be used for any type of plasma process. Non-limiting examples of other types of plasma processes include DPO (Decoupled Plasma Nitridation), RPO (Remote Plasma Oxidation) and plasma pre-cleaning processes.

It will be appreciated that use of a standard stable external light source to calibrate a spectrometer virtually eliminates any variability in measurement due to spectrometer drifts (or drifts associated with fiber optics/electronics used to collect data). According to embodiments of the invention, one or more process parameters (e.g., RF power) are used to make each process chamber read the same value or to within some defined limits for a given best known method recipe set of conditions. Thereafter, each process chamber can be monitored over time to detect any drifts in process conditions that affect properties of the substrates processed in the chambers.

Drifts can be caused by changes in any of the parameters described above. But the common ones are leak—and hence oxygen/moisture mixing with nitrogen. In the case of oxygen, or for any other species of interest, the peak emission wavelength of laser diodes and LEDS can be adjusted by changing the diode materials. Large differences in peak wavelengths are achieved by using different semiconductor systems, such as GaAlAs—GaAs for red & IR versus SiC—GaN for blue. Minor variations in peak wavelength can be achieved by adjustments in the doping levels. So diodes can be made having peak emission wavelengths corresponding to that of the oxygen emission line at 844.6 nm. With an accurate power supply, these diodes can be used to calibrate optical sensors.

In addition, helium leaks in the chamber during chucking can cause drifts. An allowable drift can be defined, after which N-dose changes will be seen. Typically, small changes do not cause sufficient drift in N-dose. According to embodiments of the invention, a process is provided in which high sensitivity to drift is provided, and the process will detect drift in plasma emission before the N-dose results measured by XPS showing drift. Accordingly, the process chamber can be proactively monitored rather than waiting for the process chamber to drift out of a controlled process state as determined by daily monitoring by end users of the process chamber.

Details of how plasma emission spectrum data can be collected and how principal component analysis can be used to identify principal components have been disclosed in commonly assigned U.S. Pat. No. 6,455,437, entitled "Method and Apparatus For Monitoring The Process State of A Semiconductor Device Fabrication Process, issued on Sep. 24, 2002, U.S. Pat. No. 6,413,867, entitled "Film Thickness Control Using Spectral Interferometry", issued on Jul. 2, 2002, U.S. Pat. No. 6,368,975, entitled "Method and Apparatus For Monitoring A Process By Employing Principal Component Analysis", issued on Apr. 9, 2002, and U.S. Pat. No. 7,169,625, entitled "Method for Automatic Determination of Semiconductor Plasma Chamber Matching and Source of Fault by Comprehensive Plasma Monitoring", issued on Jan. 30, 2007. All of the aforementioned patents are incorporated herein by reference in their entireties. According to one or more embodiments of the present invention, plasma chambers can be calibrated to an absolute standard. In these embodiments, a calibrated light source, having a reference absolute intensity, is employed to standardize one or more spectrometers. These standardized spectrometers can be utilized in different plasma chambers in different locations to match the plasma processes performed in the chambers. Utilizing such chamber matching, desirably, the resultant products produced in the different chambers conform to a predetermined and acceptable product standard. In other embodiments, a second light source is utilized to calibrate one or more spectrometers by determining the total intensity or area under the curve for a light source at one more predetermined wavelengths.

Figure 3:
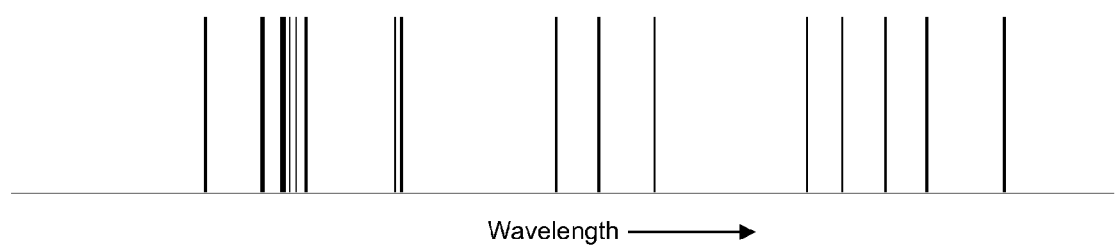
FIG. 3 shows graphical output for known wavelengths of oxygen atomic emission.

One embodiment of a process 100 is depicted in FIG. 1 as a flowchart of steps to calibrate a spectrometer using at least one standard light source. In step 102, the wavelength accuracy of a spectrometer is calibrated by measuring an emission spectrum where the radiation intensity shows peaks at well defined wavelengths from a known light source. This can be accomplished with light sources such as, but not limited to, hollow-cathode lamps, laser diodes and light emitting diodes. An example of the spectral fingerprinting used in this step can be seen in FIG. 3, which shows the discrete spectral lines from the atomic emission spectrum for the oxygen atom. (Oxygen spectra can vary depending on the excitation method and source, this is an example)

Figure 2:
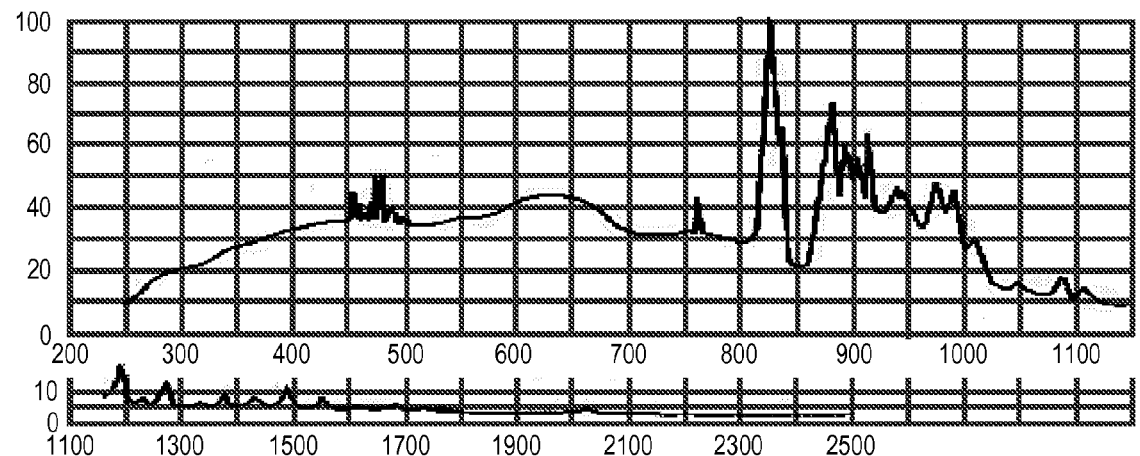
FIG. 2 shows representative electromagnetic spectrum emitted from a spectrum from a known light source, a Xenon arc lamp.

Once the spectral position of the wavelengths has been calibrated, the intensity levels at a selected range of wavelengths can be calibrated as shown in step 104 by measuring the continuum emission of a light source that has had its intensity calibrated. See FIG. 2 for an example spectrum from a continuum source, which shows the spectrum of a Xenon arc lamp. In one or more embodiments, an incandescent lamp or deuterium lamp, which has had its intensity calibrated against a primary standard black body furnace, available from the National Institute of Standards and Technology (NIST) and other sources can be used. In another embodiment, a calibrated continuum source can be used to calibrate the detector response with wavelength filters employed, thus combining steps 102 and 104 into one measurement. It should be noted that steps 102 and 104 can be performed in interchangeable order, and the number designation associated with each step is illustrative of only one embodiment of the invention. In step 106, the ratio of the peaks obtained from step 102 to the total intensity measured for the continuum source of step 104 is determined. This ratio will be used as a reference for the spectrometer. The spectrometer can be calibrated with the standardized light sources outside of the plasma processing chamber. Alternatively, the standardized light sources can be located within the plasma processing chamber. The standard light source emission would be measured by the spectrometer through a viewport in the plasma processing chamber.

Figure 4:
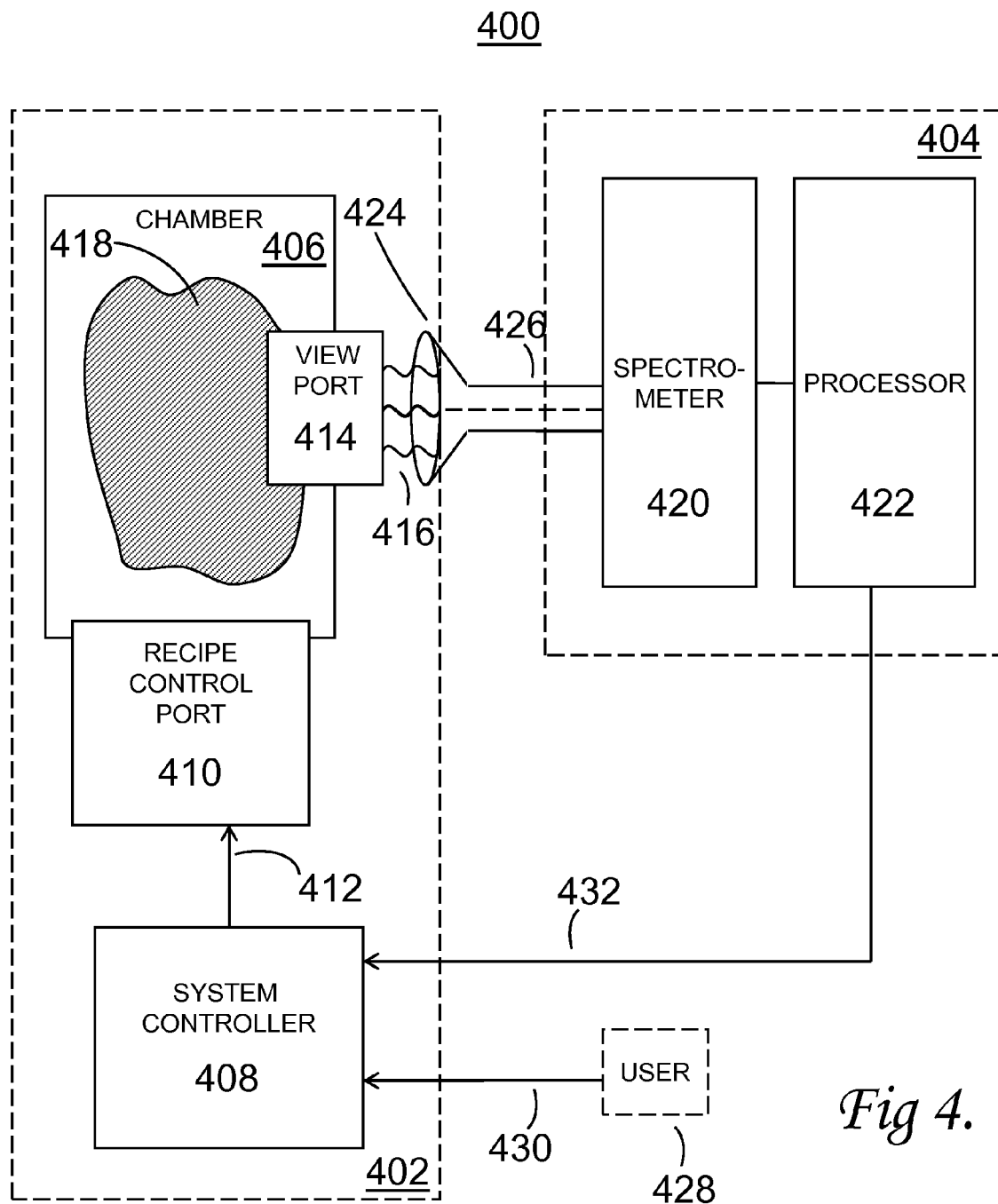
FIG. 4 is a block diagram of a processing system comprising a plasma system and a process monitoring system.

FIG. 4 is a block diagram of a processing system 400 comprising a conventional plasma etching system 402 and a process monitoring system 404 coupled thereto in accordance with an embodiment of the present invention. As used herein, "coupled" means coupled directly or indirectly. The conventional plasma processing system 402 comprises a plasma chamber 406 coupled to a plasma processing system controller 408 via a recipe control port 410 and via a first control bus 412 or other suitable interface and a process monitoring system 404. The plasma chamber 406 comprises a viewport 414 for coupling electromagnetic emissions from the inside of the chamber 406 to the outside of the chamber. The emissions are primarily optical wavelengths within the range from about 180 to 1400 nanometers, generally represented as 416 in FIG. 4. The emissions are produced by plasma 418 sustained within the plasma chamber 406. The plasma electromagnetic emissions 416 comprise emissions from a large number of plasma species (e.g., process gasses, reaction products, etc.). Note that the viewport 414 is shown positioned on the side of the plasma chamber 406, but may be positioned at any other location (e.g., on the top or bottom of the chamber 406) if desired.

The process monitoring system 404 comprises a spectrometer 420 coupled to a processor 422 in communication with system controller 408 via interface 432. The spectrometer 420 is positioned to collect the electromagnetic emissions 416 from the plasma 418 and to provide intensity information regarding a plurality of plasma electromagnetic emission wavelengths to the processor 422. A lens 424 and/or a fiber optic cable 426 are disposed between the viewport 414 and the spectrometer 420 for improving collection of the electromagnetic emissions 416 by the spectrometer 420.

In operation, a user 428 (e.g., a person in charge of a wafer fabrication process) supplies (via a second control bus 430 or other suitable interface) the plasma processing system controller 408 with a set of instructions for generating the plasma 418 within the plasma chamber 406 (i.e., a plasma recipe). Alternatively, a remote computer system for running a fabrication process may supply the plasma processing system controller 408 with a plasma recipe (e.g., as supplied by the user 428 or as stored within a plasma recipe database). A typical plasma recipe includes processing parameters such as the pressure, temperature, power, gas types, gas flow rates and the like used to initiate and maintain the plasma 418 within the plasma chamber 406 during plasma processing. Once the plasma processing system controller 408 receives a plasma recipe from the user 428, from a remote computer system, from a manufacturing execution system, etc., the plasma recipe is supplied to the recipe control port 410 via the first control bus 412, and the recipe control port 410 (or the plasma processing system controller 408 itself if the recipe control port 410 is not present) establishes and maintains within the plasma chamber 406 the processing parameters specified by the plasma recipe.

During a plasma process within the plasma chamber 406, the plasma 418 generates electromagnetic emissions 416 having wavelengths primarily in the optical spectrum (e.g., from about 180 to 1400 nanometers), although both ultraviolet and infrared wavelengths also may result. A portion of these electromagnetic emissions (e.g., the electromagnetic emissions 416) travels through the viewport 414 and reach the inventive process monitoring system 404. Note that while the electromagnetic emissions 416 are represented generally by three emission wavelengths in FIG. 1, it will be understood that the electromagnetic emissions 416 typically comprise many more wavelengths.

The spectrometer 420 receives the electromagnetic emissions 416 via the lens 424 and the fiber optic cable 426. In response thereto, the spectrometer 420 spatially separates the electromagnetic emissions 416 based on wavelength (e.g., via a prism or a diffraction grating, and generates detection signals (e.g., detection currents) for a plurality of the spatially separated wavelengths. The processor 422 continually monitors the detection signals from the spectrometer 420 and provides feedback to the system controller 408 and/or the user 428 about the plasma state. The user 428 and/or system controller 408 can adjust the processing parameters to maintain the plasma 418 in a steady state.

Another embodiment is illustrated in FIG. 5, which shows a method 500 of matching plasma states between processing chambers. Processing chambers herein may be two different processing chambers. However, processing chambers may also be a processing chamber at different moments in time. For instance, after using a processing chamber for thousands of processing cycles, its parameter settings may have drifted and the processing chamber may provide a radiation spectrum that is different from a spectrum measured at an earlier time with for instance optimal parameter settings. For that reason in one embodiment one may consider a processing chamber with optimal parameter settings as the reference chamber for the processing chamber after being used. The reference chamber in one embodiment has viewport windows which may be quartz windows that have known attenuation. In a further embodiment the reference chamber has viewport windows that are substantially unused. In a further embodiment unused quartz windows that are to be applied in a certain type of viewport in a processing chamber have substantially identical optical attenuation at predetermined wavelengths.

It should be understood that the flowchart of FIG. 5 does not require steps to be performed sequentially but has been created as a convenient means of describing aspects of the invention. Step 502 involves the calibration of a spectrometer, as discussed above with respect to FIG. 1. In step 504, a reference plasma processing chamber is employed to process a substrate with the desired plasma recipe. The optical emission spectra of the plasma are monitored throughout the processing. The ratio of the intensities of the selected wavelengths to the total intensity is determined. These ratios are used as a marker of the characteristics of the reference process. A substrate is processed using a chamber other than the reference chamber in step 506. The same plasma recipe as that of 504 is employed with the second chamber and the OES is collected. The same characteristic wavelength ratios are determined as with the reference chamber processing. The surface characteristics of processed substrates from 504 and 506 are measured in 508. These characteristics include, but are not limited to, the degree of nitrogen dosing or oxygen dosing. The surface characteristics are typically measured by x-ray photoelectron spectroscopy, but other techniques can be used as appropriate. The wavelength ratios are correlated to the surface characteristics for the second substrates and compared to the correlation from the reference process in 510. The operating parameters of the processing chamber are modified in 512, one at a time, and a substrate is processed. The OES data and surface characteristics are measured for each modified operating condition. Using the correlated data from the modified conditions 512, the sensitivity to each parameter is determined 514. The appropriate parameter(s) are modified 516 on the second chamber to obtain the same surface characteristics as that of the reference chamber.

As a specific example of the process immediately described above, two external lights sources are provided to calibrate a spectrometer for a DPN process to measure nitridation of substrates. For the first light source, the total intensity (area under the curve is calculated, and for the second light source, the intensities of selected peaks, area under each peak and ratios of selected peaks are calculated for known light sources. The calibrated spectrometer is then used on a DPN chamber for two best known conditions: (1) 200 W, CW, 30 s, 20 MT, 5 SLM nitrogen and no chucking and (2) 1000 W, 5% duty cycle, 20 mT, 30 s and 5 SLM of nitrogen. It will of course be recognized, that these two conditions are exemplary only. Spectra for the two conditions are collected and the area under key species peaks are expressed as a fraction of (i) peak close to wavelength in reference for the second source and also as a total fraction of the total area for the first source.

The same procedure is then repeated on another DPN chamber with the same recipe conditions, and the same spectra are collected and the area under key species are expressed the same way as in the reference chamber. The differences between the two chambers in calculated values using the spectra and XPS N-dos data are determined, and differences (if any) between the two chambers are correlated. Then, parameters for the second chamber are varied on at a time, for example, power, pressure, reflected power, nitrogen flow, He leak amount, moisture content variation, etc. Differences between in calculated values using the spectra and XPS N-does are determined, and sensitivities are correlated. Using the sensitivities to each of the parameters, a method for chamber matching can be implemented. For example, if two chambers differ by 5% in XPS N-dose, the power, pressure or other parameter can be adjusted by a certain amount. The actual adjustment must be based on data from each tool/chamber. If the forward power from each chamber in the process step is different, then the powers must be adjusted. If the reflected power in one chamber is high, the recipe can be tuned to lower the reflected power. If the powers are determined to be the same, another parameter, for example, pressure, He leak, etc. can be investigated until the source of difference is corrected and the second chamber matches the reference chamber. This concept can be extended to additional chambers so that chambers can all be matched to a standard reference chamber. If the chambers are still not matched with XPS N-dose, even after allowing a defined offsets in power are allowed using the RF Calibration Tables, then parameters outside DPN chamber can be investigated such as leaks in a rapid thermal processing (RTP) chamber step prior to DPN or wafer temperature coming out of RTP chamber, or leaks in PNA chamber or metrology queue time. Eventually, the source of process discontinuity can be identified until the second and subsequent processes are calibrated to the substrates produced according to the reference process.

One phenomenon that may adversely affect the matching of two different chambers or of one chamber at two different moments in time is the change in optical path of the plasma radiation over time. A significant aspect of radiation attenuation is the window in the viewport of the chamber through which a detector such as a spectrometer will measure radiation. Over time the different steps of etching and deposition may affect the attenuation of a window in the viewport, which may be a quartz window. For instance, an attenuation of transmission of radiation of a certain wavelength through a window may have increased after the chamber has gone through a number of processing cycles. Such a chamber may be called an aged chamber. One may have measured through a viewport of a chamber in operation the intensity of a radiation at a certain wavelength generated by a plasma when the chamber was substantially new or refurbished or with substantially unused windows. Assume that one measures again through the viewport of the chamber in operation an intensity of a radiation at the same wavelength generated by a plasma when the chamber has gone through several thousands of processing cycles. This may lead to a measurement of intensity that is below the measured intensity when the chamber was new or in a reference state.

A question that has to be addressed is if the lower intensity is caused by change in process settings or chamber leaks and thus by a resulting lower intensity of generated plasma radiation or if the lower measured intensity is caused by an increased attenuation of the quartz window, or perhaps by both. In accordance with an aspect of the present invention a method is provided that helps determine if a change of measured intensity was caused by increased attenuation in an optical path, by changed processing conditions or by both. In accordance with a further aspect of the present invention a method is provided that corrects a measured plasma radiation according to changes in attenuation and that allows adjustment of one or more operational parameter settings to match a reference setting. In accordance with a further aspect of the present invention a system is provided that can implement the adjustment method. In accordance with yet a further aspect of the present invention a kit is provided that enables a user to measure changes in attenuation of an optical path and to adjust operational settings of a chamber using the kit.

It was shown above that spectra measured from radiation of a plasma are good indicators of a performance of a processing chamber. When one is sure that a correct spectrum is measured and that the measured spectrum is not identical to a reference spectrum one may make adjustments to operational parameter settings to make the performance of the chamber substantially identical to the performance of a reference chamber. The requirement is to provide a method of correction to a measured spectrum that will eliminate the effect of change in the optical path which includes a viewport.

In accordance with an aspect of the present invention one may calibrate a detector with a radiation source. One may use a radiation source with a discrete radiation such as a laser. One may select a source that has its discrete wavelength coinciding with a spectrum peak in the plasma radiation. A detector may be a spectrometer that will be calibrated against the radiation source. For instance one may detect the radiation from a standardized source in a direct radiation path with no windows with a spectrometer. One may then detect with the detector an intensity from the radiation source through an optical path having a new or unused window. Next, one may determine with the detector an intensity from the radiation source through an optical path having a used window. One may determine a correction factor to offset the attenuation of the used window. This correction factor is related to a spectrum from a standardized source measured through a reference path and an aged path in the chamber. Both paths also relate to measured spectra generated by a plasma. The correction factor determined from a standardized radiation source may be correlated with a spectrum measured from a plasma.

It was stated before that spectra measured from a plasma in an operational processing chamber show a high level of repeatability. The measured spectra depend on the settings of operational parameters. In case of measuring a spectrum from a plasma in a chamber with a used window that may have experienced an increase in attenuation, one may adjust the measured radiation intensity with the correction factor that was determined by using a standardized source. In one embodiment one has to multiply the measured intensity from a radiation measured through an optical path having a used window with the correction factor to arrive at the intensity that one would measure by using the same radiation source with an optical transmission path with an unused window. One may thus multiply a spectrum intensity measured from a plasma in a chamber with the used window with the correction factor to arrive at the intensity that would have been measured by using an unused window in the optical transmission path.

One also has a reference spectrum intensity measured from a plasma in a chamber with a substantially unused window. One may thus compare the intensity of a reference spectrum with an intensity of a spectrum measured from a plasma in a chamber with a used window by multiplying the measured intensity with the correction factor. If the reference intensity and the corrected measured intensity are identical the processes in the two chambers may assumed to be identical. If the reference and corrected measured intensities are not identical one may assume that conditions of the process chamber have changed and adjust the operation parameters as described earlier to match the performance of the chamber with a reference chamber.

A description has been provided using a single narrow band discrete radiation source. One may also apply multiple discrete sources and determine multiple correction factors. One may also use a continuous radiation source. To determine dependency of attenuation changes on wavelength one may apply a tunable detector or one may use narrow band filters combined with different standardized single wavelength sources or with a standardized broadband radiation source. Specific changes in corrected spectrum intensities at different wavelengths may provide information on how the conditions in a chamber have changed. It may also suggest how to change operational parameter settings to achieve a setting matching a reference chamber. Additional information may be gathered by measuring spectra in the reference and the aged chamber by applying different power settings of the chamber.

Figure 6:
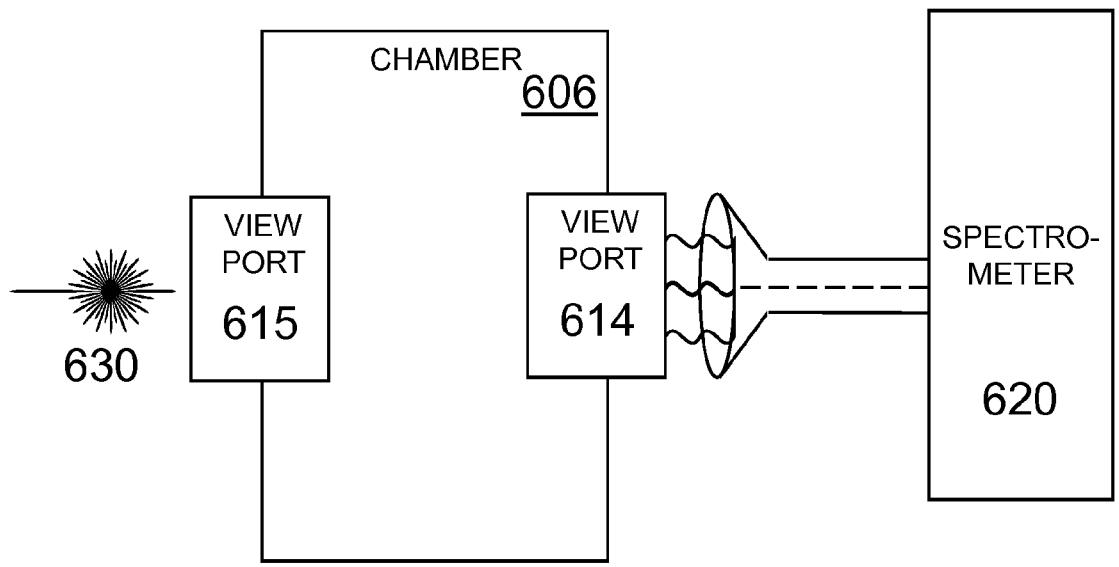
FIG. 6 is a block diagram of a processing system illustrating the use of a laser to measure radiation through two viewports.

A possible drawback of using a single window to determine a correction factor for a changed optical transmission path is that the radiation source has to be inside the chamber. In general that means that the chamber has to be opened. In accordance with another aspect of the present invention two aligned viewports each having a window may be used to determine a correction factor for one window. For instance chamber aging may affect attenuation in aligned windows in different viewports equally. In that case one may assign half the correction factor of the two aligned viewports to a single viewport. An arrangement in accordance with that aspect is shown in FIG. 6. FIG. 6 shows in diagram a processing chamber 606 not in operation and thus without a plasma which is a slightly modified version of FIG. 4. The chamber has two viewports 614 and 615 each of which may contain a quartz window. The quartz windows may have been exposed to repeated etching and deposition and may now have an attenuation that is substantially different from their unused condition. A spectrometer 620 is used to measure radiation. The spectrometer may be kinematically fixed to a window and apply a lens and optical fiber to collect radiation. A radiation source 630, which may be a laser is used to have the spectrometer 620 measure an intensity.

Figure 7:
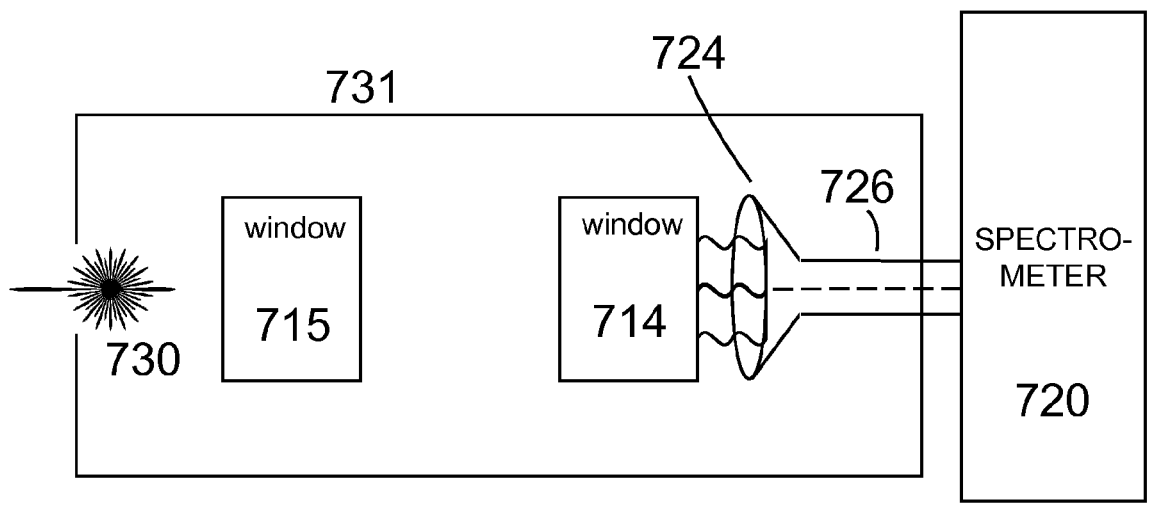
FIG. 7 is a block diagram of a kit illustrating the use of a laser to measure radiation through two windows outside a processing system.

FIG. 7 shows a diagram of an arrangement that can be used to measure a baseline intensity for determining a correction factor. The arrangement has two unused quartz windows 714 and 715 and a source 730 which may be the same source as 630 in FIG. 6. A detector 720 which may be the spectrometer 620 is attached to window 714. Furthermore, the arrangement may include the same potentially kinematic attachment of the detector to the window 714 as the attachment of the viewport in FIG. 6 to the spectrometer 620. If different detectors and attachments such as a lens 724 and/or optical fiber 726 or none are used the effect of these attachments or their absence have to be taken into account in the correction factor and have to be accounted for in a calibration step. To make sure that effects of positioning and distance are accounted for a construction 731 may be used that holds all optical components in substantially the same position for instance as compared to corresponding positions in FIG. 6.

One may provide a kit comprising at least one unused window, a radiation source and a detector for determining a correction factor. The kit may also comprise two or more unused windows. The kit may also comprise a structure for fixating a position of a radiation source, one or more windows and a detector. The kit may also comprise two or more radiation sources. The kit may also comprise a continuous radiation source that radiates over a broad range of wavelengths. The kit may also comprise a table which assists in determining operational parameter settings. Such a table may have as an input a measured intensity and may provide as a result a correction factor. It may also have as an output a number representing a parameter setting or a recommendation for changing a parameter setting of the process chamber. The table may be included in the kit as a printed table. It may also provide a table stored in a memory readable by a computing device. The table may also be implemented in a computing device as an algorithm that can be executed by the computing device.

Figure 8:
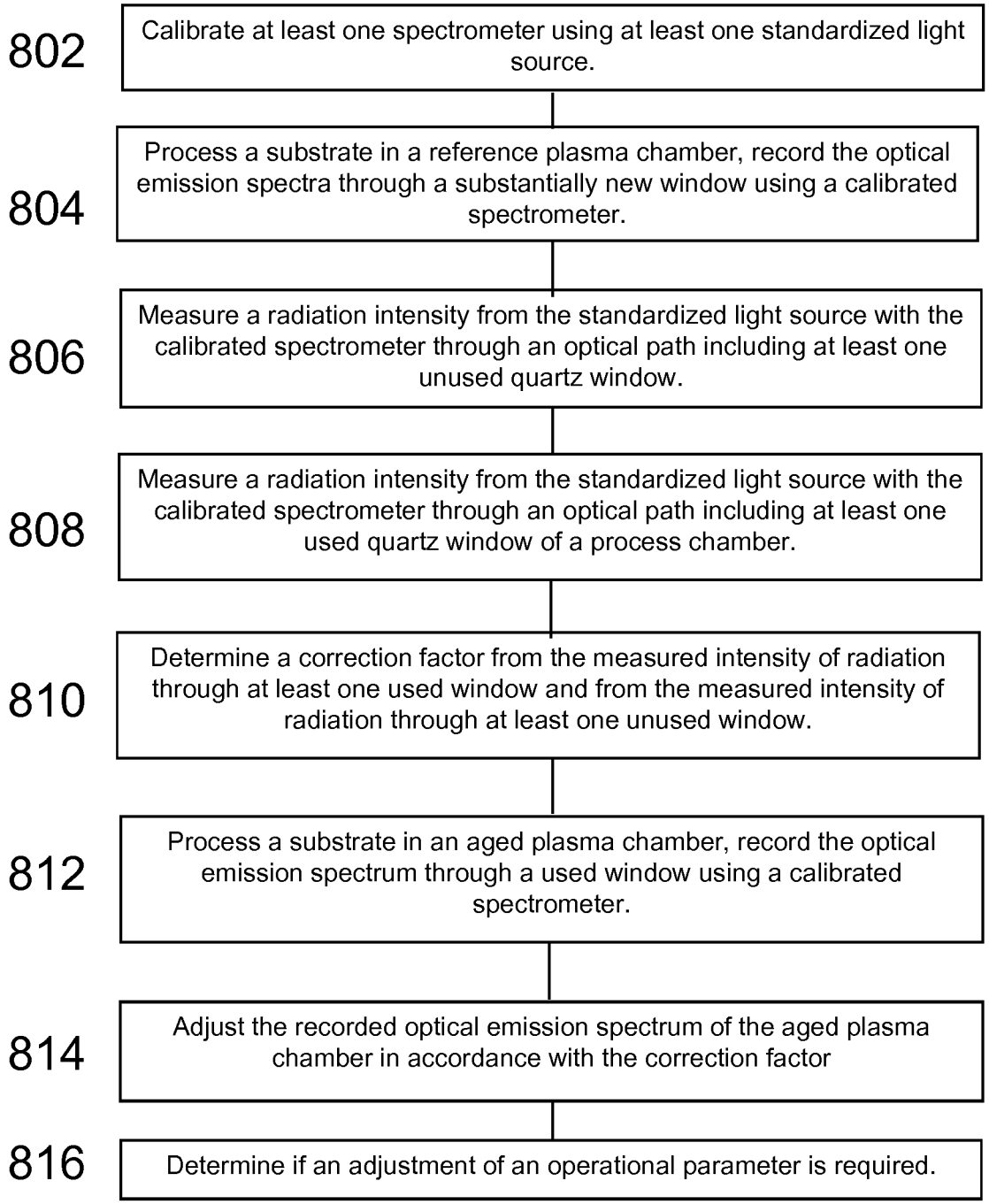
FIG. 8 is a flowchart illustrating steps of a method of plasma stability monitoring in accordance with an aspect of the present invention.

A further embodiment is illustrated in FIG. 8, which shows the flowchart 800 for a method of monitoring the plasma stability of a processing chamber. A spectrometer calibrated with a standardized light source 802 is required. A substrate is processed in step 804 using the plasma chamber that will be monitored. The chamber will have a substantially unused quartz window through which the spectrum or a component of a spectrum is recorded using the calibrated spectrometer. The chamber at this stage has operational settings that will serve as the reference settings and that are associated with the measured spectrum or a component thereof. Using the standardized radiation source an intensity is measured in step 806 of radiation through an optical path containing at least one substantially unused quartz window with the calibrated spectrometer. One may measure the intensity through the unused window of the chamber, before aging of the chamber. One may also measure the intensity using an unused quartz window that may be provided as part of a kit. In the latter case one may measure or re-measure the intensity through an unused window at any convenient time. In step 808 one measures an intensity of radiation from the standardized radiation source with the calibrated spectrometer through an optical path that contains at least one quartz window that has been used in the aging chamber. In step 810 one determines a correction factor from the two intensity measurements with the standardized source. In step 812 a substrate is processed in the aged plasma chamber. The chamber will have the used quartz window through which the spectrum or a component of a spectrum is recorded using the calibrated spectrometer. In step 814 the measured spectrum or component of the spectrum through the aged or used window is adjusted with the correction factor of step 810. In step 816 one may determine if adjustment of a parameter setting is required. If the spectrum adjusted with correction factor in step 814 is substantially identical to the recorded spectrum or component of step 804 then one may conclude in step 816 that any change in measured spectra was due to changes in for instance attenuation of a window. If the results of step 804 and 814 are substantially different then one may conclude that operational changes in the chamber have occurred. Based on magnitude of changes and direction of changes such as increase or decrease one may modify a parameter setting based on for instance a modification table. One may monitor different components in a spectrum. Relative changes in components of a spectrum may provide additional information on how to change operational parameter settings of the chamber. The modification table may be implemented as a printed table or as a computer memory stored table that can be read by a computing device. A table or part of a table may also be implemented as an algorithm that can be executed by a computing device, for instance to determine table values and/or parameter settings by interpolation.

Methods provided herein as an aspect of the present invention may also be implemented in a system. A system has at least a memory to store and to retrieve data and instructions, and a processor enabled to retrieve instructions from the memory and to execute instructions to perform the steps of the methods disclosed herein in accordance with one or more aspects of the present invention. Such a system may be a separate system. It may also be part of the system as described in FIG. 4. For instance, one may measure radiation from a standardized source through a viewport 414 and store the result in a memory or a storage medium which may be controlled by a system controller 408. The user 428 may inform the controller that a specific measurement should be stored as a reference result of a standardized source. Once the chamber has its initial optimal setting the result from a plasma spectrum may also be stored and controlled by the system controller 408. The corresponding parameter settings may also be stored. Over time the system controller will record plasma spectrum measurements from spectrometer 420. At a certain time a user 428 may indicate that a measurement is again from a standardized source now involving used windows. A user may also enter manually those measurement results into the system controller. The system controller may be programmed to calculate a correction factor and apply the correction factor to a recent plasma spectrum and compare the result to the stored reference spectrum. Using a table, an algorithm or both the system may determine if chamber conditions have changed compared to reference conditions. The system may provide an alert to a user informing the user of changed or unchanged conditions. The system may also provide recommendations for new parameter settings. The system may also automatically enter new parameter settings.

Techniques for matching a newly manufactured or newly maintained plasma chamber to an absolute reference are desired in the semiconductor processing field. Additionally, methods to monitor the performance of a plasma chamber over a period of usage are needed for maintaining process repeatability and control.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

We claim:

1. A kit for adjusting an operational parameter setting in a substrate processing chamber, comprising:
    a radiation source having a wavelength that is representative of a plasma spectrum generated in a chamber;
    a calibrated radiation detector, calibrated to the radiation source;
    a reference optical window having a known attenuation at the wavelength from the radiation source; and
    an adjustment table to adjust the operational parameter of the substrate processing chamber based on a correction factor determined from a measured optical intensity of the radiation source through the reference optical window compared to a measured optical intensity of the radiation source through a used chamber window, where the operational parameter is modified in accordance with the correction factor.

2. The kit as claimed in claim 1, further comprising a structure to fix a position of the radiation source, the reference optical window and the calibrated radiation detector.

3. The kit as claimed in claim 1, wherein the adjustment table is implemented in a computing device.

4. The kit as claimed in claim 1, wherein the wavelength of the radiation source is at a discrete wavelength that coincides with a spectrum peak in the plasma radiation.

5. The kit as claimed in claim 1, wherein the radiation source is a single narrow band discrete radiation source.

6. The kit as claimed in claim 5, which further comprises multiple discrete sources.

7. The kit as claimed in claim 1, wherein the radiation source is a standardized broadband radiation source.

8. The kit as claimed in claim 1, wherein the radiation source, reference optical window, and calibrated radiation detector form an optical path for measuring an optical intensity through the reference optical window.

* * * * *